(12) United States Patent
Bangel et al.

(10) Patent No.: US 9,232,795 B2
(45) Date of Patent: Jan. 12, 2016

(54) HERBICIDAL COMPOSITIONS COMPRISING 4-AMINO-3-CHLORO-6-(4-CHLORO-2-FLUORO-3-METHOXYPHENYL) PYRIDINE-2-CARBOXYLIC ACID OR A DERIVATIVE THEREOF AND FLURTAMONE

(71) Applicants: Bryston L. Bangel, Camby, IN (US); Norbert M. Satchivi, Carmel, IN (US)

(72) Inventors: Bryston L. Bangel, Camby, IN (US); Norbert M. Satchivi, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/134,434

(22) Filed: Dec. 19, 2013

(65) Prior Publication Data

US 2014/0179524 A1    Jun. 26, 2014

Related U.S. Application Data

(60) Provisional application No. 61/745,044, filed on Dec. 21, 2012.

(51) Int. Cl.
    *A01N 43/40* (2006.01)
    *A01N 43/08* (2006.01)

(52) U.S. Cl.
    CPC ............... *A01N 43/40* (2013.01); *A01N 43/08* (2013.01)

(58) Field of Classification Search
    None
    See application file for complete search history.

(56) References Cited

U.S. PATENT DOCUMENTS

| | | | |
|---|---|---|---|
| 7,314,849 B2 * | 1/2008 | Balko et al. | 504/244 |
| 2008/0045734 A1 | 2/2008 | Balko et al. | |
| 2009/0062121 A1 | 3/2009 | Satchivi et al. | |
| 2011/0092367 A1 | 4/2011 | Griveau et al. | |
| 2011/0287932 A1 * | 11/2011 | Hacker et al. | 504/103 |

FOREIGN PATENT DOCUMENTS

WO  PCT/US2013/076439    4/2014

* cited by examiner

*Primary Examiner* — Alton Pryor
(74) *Attorney, Agent, or Firm* — Michael J. Terapane

(57) ABSTRACT

Provided herein are herbicidal compositions and methods employing combinations of (a) a compound of formula (I):

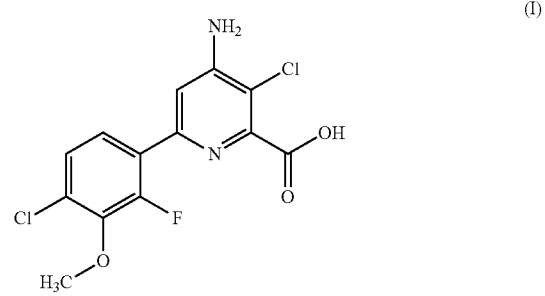

or an agriculturally acceptable salt or ester thereof and (b) flurtamone. In certain embodiments the combinations include flufenacet or diflufenican as a third herbicidally active component.

31 Claims, No Drawings

HERBICIDAL COMPOSITIONS COMPRISING 4-AMINO-3-CHLORO-6-(4-CHLORO-2-FLUORO-3-METHOXYPHENYL)PYRIDINE-2-CARBOXYLIC ACID OR A DERIVATIVE THEREOF AND FLURTAMONE

CROSS REFERENCE TO RELATED APPLICATIONS

This application claims the benefit of U.S. Provisional Patent Application Ser. No. 61/745,044 filed Dec. 21, 2012, the disclosure of which is expressly incorporated herein by reference.

BACKGROUND

The protection of crops from weeds and other vegetation which inhibit crop growth is a constantly recurring problem in agriculture. To help combat this problem, researchers in the field of synthetic chemistry have produced an extensive variety of chemicals and chemical formulations effective in the control of such unwanted growth. Chemical herbicides of many types have been disclosed in the literature and a large number are in commercial use. However, there remains a need for compositions and methods that are effective in controlling undesirable vegetation.

US 2011/0287932 discloses specific three component herbicidal compositions consisting of glufosinate ammonium, methyl 4-amino-3-chloro-6-(4-chloro-2-fluoro-3-methoxyphenyl)-pyridine-2-carboxylate, with (1) flurtamone to control *Matricaria chamomilla* in glufosinate tolerant wheat (Table 4), or (2) diflufenican to control volunteer *Brassica napus* in glufosinate tolerant wheat (Table 6), or (3) flufenacet to control *Setaria viridis* in glufosinate tolerant wheat.

US 2009/0062121 discloses specific herbicidal compositions consisting of methyl 4-amino-3-chloro-6-(4-chloro-2-fluoro-3-methoxyphenyl)-pyridine-2-carboxylate and diflufenican (Tables 1 and 23), specific herbicidal compositions consisting of the potassium salt of 4-amino-3-chloro-6-(4-chloro-2-fluoro-3-methoxyphenyl)-pyridine-2-carboxylic acid and diflufenican (Table 60), and specific herbicidal compositions consisting of methyl 4-amino-3-chloro-6-(4-chloro-2-fluoro-3-methoxyphenyl)-pyridine-2-carboxylate, diflufenican, and flufenacet (Tables 2 and 24).

SUMMARY

Provided herein are herbicidal compositions comprising a herbicidally effective amount of a combination of (a) a compound of the formula (I)

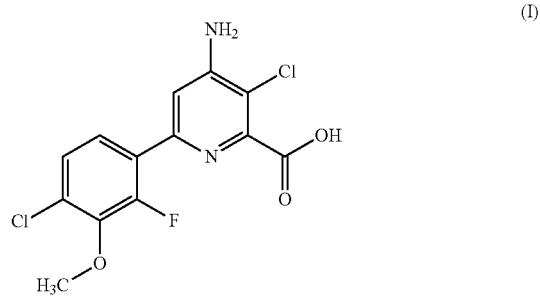 [SMILES: COc1c(Cl)ccc(-c2cc(N)c(Cl)c(C(=O)O)n2)c1F]

or an agriculturally acceptable salt or ester of thereof, and (b) flurtamone, with the proviso that the composition does not contain glufosinate, L-glufosinate, or bialaphos. In some embodiments the compositions contain (a) a compound of the formula (I) or an agriculturally acceptable salt or ester of thereof, flurtamone, diflufenican, and flufenacet. The compositions may also contain an agriculturally acceptable adjuvant or carrier.

Provided herein are also methods of controlling undesirable vegetation comprising applying to an area where control is desired (a) a compound of formula (I) or an agriculturally acceptable ester or salt thereof and (b) flurtamone, with the proviso that no glufosinate, L-glufosinate, or bialaphos is also applied. In some embodiments both diflufenican and flufenacet are applied with the compound of formula (I) or an agriculturally acceptable ester or salt thereof. In some embodiments the combination is applied to the vegetation or the locus thereof. In some embodiments the combination is applied to soil or water to prevent the emergence or growth of the vegetation.

DETAILED DESCRIPTION

Definitions

As used herein, the compound of formula (I) has the following structure:

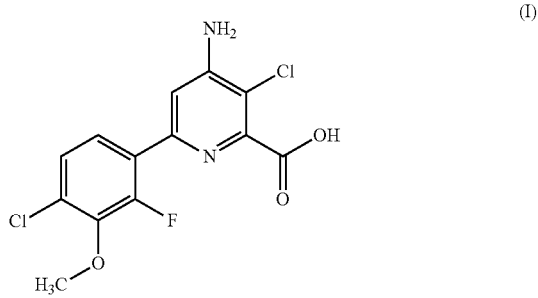 [SMILES: COc1c(Cl)ccc(-c2cc(N)c(Cl)c(C(=O)O)n2)c1F]

The compound of formula (I) can be identified by the name 4-amino-3-chloro-6-(4-chloro-2-fluoro-3-methoxyphenyl)-pyridine-2-carboxylic acid and has been described in U.S. Pat. No. 7,314,849 (B2), which is incorporated herein by reference in its entirety. An exemplary ester of the compound of formula (I) is the methyl ester. Exemplary uses of the compound of the formula (I) include controlling undesirable vegetation, including grass, broadleaf and sedge weeds, in multiple non-crop and cropping situations.

As used herein, flurtamone is (±)-5-(methylamino)-2-phenyl-4-[3-(trifluoromethyl)phenyl]-3(2H)-furanone. Its herbicidal activity is exemplified in Tomlin, C. D. S., Ed. *The Pesticide Manual: A World Compendium*, 15$^{th}$ ed.; BCPC: Alton, 2009 (hereafter "*The Pesticide Manual*, Fifteenth Edition, 2009"). Exemplary uses of flurtamone include its use for pre-plant incorporated, pre-emergence or post-emergence control of broad-leaved and some grass weeds in small grains, peanuts, cotton, peas and sunflowers.

As used herein, diflufenican is N-(2,4-difluorophenyl)-2-[3-(trifluromethyl)phenoxy]-3-pyridinecarboxamide. As described in *The Pesticide Manual*, Fifteenth Edition, 2009, page 362, diflufenican is a selective contact and residual herbicide that is used pre- and early post-emergence in autumn-sown wheat and barley to control grass and broad-leaved weeds. It is typically used in combination with other cereal herbicides, e.g. flufenacet.

As used herein, flufenacet is N-(4-fluorophenyl)-N-(1-methylethyl)-2-[[5-(trifluoromethyl)-1,3,4-thiadiazol-2-yl]oxy]acetamide. As described in *The Pesticide Manual*, Fifteenth Edition, 2009, page 522, flufenacet is a systemic herbicide used, for example, post-emergence in corn/maize, wheat, and rice.

As used herein, herbicide or herbicidal active ingredient means a compound, i.e., an active ingredient that kills, controls or otherwise adversely modifies the growth of plants, e.g., causing deviations from natural development, killing, effecting regulation, causing desiccation, causing retardation, and the like.

As used herein, a herbicidally effective or vegetation controlling amount is an amount of active ingredient which causes an adversely modifying effect to the vegetation e.g., causing deviations from natural development, killing, effecting regulation, causing desiccation, causing retardation, and the like.

As used herein, controlling undesirable vegetation means preventing, reducing, killing, or otherwise adversely modifying the development of plants and vegetation. Described herein are methods of controlling undesirable vegetation through the application of certain herbicide combinations or compositions. Methods of application include, but are not limited to applications to the vegetation or locus thereof, e.g., application to the area adjacent to the vegetation, as well as pre-emergence, post-emergence, foliar, and in-water applications.

As used herein, plants and vegetation include, but are not limited to, germinant seeds, emerging seedlings, plants emerging from vegetative propagules, immature vegetation, and established vegetation.

As used herein, agriculturally acceptable salts and esters refer to salts and esters that exhibit herbicidal activity, or that are or can be converted in plants, water, or soil to the referenced herbicide. Exemplary agriculturally acceptable esters are those that are or can by hydrolyzed, oxidized, metabolized, or otherwise converted, e.g., in plants, water, or soil, to the corresponding carboxylic acid which, depending upon the pH, may be in the dissociated or undissociated form.

Exemplary salts include those derived from alkali or alkaline earth metals and those derived from ammonia and amines. Exemplary cations include sodium, potassium, magnesium, and aminium cations of the formula:

$R^1R^2R^3R^4N^+$ wherein $R^1$, $R^2$, $R^3$ and $R^4$ each, independently represents hydrogen or $C_1$-$C_{12}$ alkyl, $C_3$-$C_{12}$ alkenyl or $C_3$-$C_{12}$ alkynyl, each of which is optionally substituted by one or more hydroxy, $C_1$-$C_4$ alkoxy, $C_1$-$C_4$ alkylthio or phenyl groups, provided that $R^1$, $R^2$, $R^3$ and $R^4$ are sterically compatible. Additionally, any two of $R^1$, $R^2$, $R^3$ and $R^4$ together may represent an aliphatic difunctional moiety containing one to twelve carbon atoms and up to two oxygen or sulfur atoms. Salts can be prepared by treatment with a metal hydroxide, such as sodium hydroxide, with an amine, such as ammonia, trimethylamine, diethanolamine, 2-methylthiopropylamine, bisallylamine, 2-butoxyethylamine, morpholine, cyclododecylamine, or benzylamine or with a tetraalkylammonium hydroxide, such as tetramethylammonium hydroxide or choline hydroxide.

Exemplary esters include those derived from $C_1$-$C_{12}$ alkyl, $C_3$-$C_{12}$ alkenyl, $C_3$-$C_{12}$ alkynyl or $C_7$-$C_{10}$ aryl-substituted alkyl alcohols, such as methyl alcohol, isopropyl alcohol, 1-butanol, 2-ethylhexanol, butoxyethanol, methoxypropanol, allyl alcohol, propargyl alcohol, cyclohexanol or unsubstituted or substituted benzyl alcohols. Benzyl alcohols may be substituted with from 1-3 substituents independently selected from halogen, $C_1$-$C_4$ alkyl or $C_1$-$C_4$ alkoxy. Esters can be prepared by coupling of the acids with the alcohol using any number of suitable activating agents such as those used for peptide couplings such as dicyclohexylcarbodiimide (DCC) or carbonyl diimidazole (CDI); by reacting the acids with alkylating agents such as alkylhalides or alkylsulfonates in the presence of a base such as triethylamine or lithium carbonate; by reacting the corresponding acid chloride of an acid with an appropriate alcohol; by reacting the corresponding acid with an appropriate alcohol in the presence of an acid catalyst or by transesterification.

Compositions and Methods

Provided herein are herbicidal compositions comprising a herbicidally effective amount of (a) a compound of the formula (I)

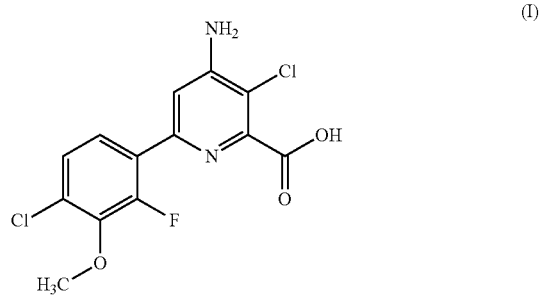 [SMILES: COc1c(Cl)ccc(-c2cc(N)c(Cl)c(C(=O)O)n2)c1F]

(I)

or an agriculturally acceptable salt or ester of thereof and (b) flurtamone, with the proviso that the composition does not contain glufosinate, L-glufosinate, or bialaphos.

Also provided are herbicidal compositions comprising a herbicidally effective amount of (a) a compound of the formula (I) or an agriculturally acceptable salt or ester of thereof, (b) flurtamone and (c) diflufenican or flufenacet. In certain embodiments, the composition comprises (a) the compound of formula (I) or an agriculturally acceptable salt or ester thereof, (b) flurtamone and (c) flufenacet. In certain embodiments, the composition comprises (a) the compound of formula (I) or an agriculturally acceptable salt or ester thereof, (b) flurtamone and (c) diflufenican.

Also provided are methods of controlling undesirable vegetation comprising applying to an area where control is desired a herbicidally effective amount of a combination comprising the compound of formula (I) or an agriculturally acceptable salt or ester thereof and (b) flurtamone, with the proviso that the combination does not contain glufosinate, L-glufosinate, or bialaphos. In certain embodiments, the combination comprises (a) the compound of formula (I) or an agriculturally acceptable salt or ester thereof, (b) flurtamone, and (c) flufenacet. In certain embodiments, the combination comprises (a) the compound of formula (I) or an agriculturally acceptable salt or ester thereof, (b) flurtamone, and (c) diflufenican.

Furthermore, in some embodiments, the two component and three component combinations described above exhibit synergism, e.g., the herbicidal active ingredients are more effective in combination than when applied individually. Synergism has been defined as "an interaction of two or more factors such that the effect when combined is greater than the predicted effect based on the response of each factor applied separately." Senseman, S., Eed. Herbicide Handbook. $9^{th}$ ed.

Lawrence: Weed Science Society of America, 2007. In certain embodiments, the compositions exhibit synergy as determined by the Colby equation (Colby, S. R. Calculation of the synergistic and antagonistic response of herbicide combinations. *Weeds* 1967, 15, 20-22).

More specifically, the following equation is used to calculate the expected activity of mixtures containing two herbicidal active ingredients:

$$\text{Expected} = A + B - (A \times B/100)$$

A=observed efficacy of a first active ingredient at the same concentration as used in the mixture;
B=observed efficacy of the second active ingredient (or product, which may contain a combination of active ingredients) at the same concentration as used in the mixture.
For mixtures containing three herbicidal active ingredients, the following equation can be used to calculate the expected activity:

$$\text{Expected} = 100 - [(100-A)(100-B)(100-C)/10{,}000]$$

A=observed efficacy of a first active ingredient at the same concentration as used in the mixture;
B=observed efficacy of a second active ingredient B at the same concentration as used in the mixture;
C=observed efficacy of a third active ingredient C at the same concentration as used in the mixture.

In certain embodiments of the compositions and methods described herein, the compound of formula (I), i.e., the carboxylic acid, is employed. In certain embodiments, a carboxylate salt, e.g. the potassium salt, of the compound of formula (I) is employed. In certain embodiments, an arylalkyl or alkyl ester is employed. In certain embodiments, a benzyl, substituted benzyl, or $C_1$-$C_4$ alkyl, e.g., n-butyl ester, is employed. In certain embodiments, the methyl ester or potassium salt is employed.

In some embodiments, the herbicidal active ingredients are formulated in one composition, tank mixed, applied simultaneously, or applied sequentially.

Herbicidal activity is exhibited by the herbicidal compositions when they are applied directly to the plant or to the locus of the plant at any stage of growth. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted to promote non-selective or selective herbicidal action. In some embodiments, the compositions described herein are applied as a post-emergence application, pre-emergence application, or in-water application to flooded paddy rice or water bodies (e.g., ponds, lakes and streams), to relatively immature undesirable vegetation to achieve the maximum control of weeds.

In some embodiments, the compositions and methods provided herein are utilized to control weeds in crops, e.g. cereal crops, including but not limited to direct-seeded, water-seeded and transplanted rice, wheat, barley, triticale, oats, rye, and corn/maize, and in pastures, grasslands, rangelands, fallowland, industrial vegetation management (IVM) and rights-of-way.

In certain embodiments, the compositions and methods provided herein are utilized to control weeds in rice. In certain embodiments, the rice is direct seeded, water-seeded, or transplanted rice.

The compositions and methods described herein may be used to control undesirable vegetation on glyphosate-tolerant-, glufosinate-tolerant-, dicamba-tolerant-, phenoxy auxin-tolerant-, pyridyloxy auxin-tolerant-, aryloxyphenoxypropionate-tolerant-, acetyl CoA carboxylase (ACCase) inhibitor-tolerant-, imidazolinone-tolerant-, acetolactate synthase (ALS) inhibitor-tolerant-, 4-hydroxyphenyl-pyruvate dioxygenase (HPPD) inhibitor-tolerant-, protoporphyrinogen oxidase (PPO) inhibitor-tolerant-, triazine-tolerant-, bromoxynil-tolerant-crops, for example, in conjunction with glyphosate, dicamba, phenoxy auxins, pyridyloxy auxins, aryloxyphenoxypropionates, ACCase inhibitors, imidazolinones, ALS inhibitors, HPPD inhibitors, PPO inhibitors, triazines, and bromoxynil The compositions and methods may be used in controlling undesirable vegetation in crops possessing multiple or stacked traits conferring tolerance to multiple chemistries and/or inhibitors of multiple modes-of-action. In some embodiments, the compound of formula (I) or salt or ester thereof and complementary herbicide or salt or ester thereof are used in combination with herbicides that are selective for the crop being treated and which complement the spectrum of weeds controlled by these compounds at the application rate employed. In some embodiments, the compositions described herein and other complementary herbicides are applied at the same time, either as a combination formulation or as a tank mix.

The compositions and methods provided herein are utilized to control undesirable vegetation. Undesirable vegetation includes, but is not limited to, undesirable vegetation that occurs in rice, cereals, range and pasture, and non-crop settings, (e.g., rights-of-way, IVM).

In some embodiments, the methods provided herein are utilized to control undesirable vegetation in cereals. In certain embodiments, the undesirable vegetation is *Alopecurus myosuroides* Huds. (blackgrass, ALOMY), *Apera spica-venti* (L.) Beauv. (windgrass, APESV), *Avena fatua* L. (wild oat, AVEFA), *Bromus tectorum* L. (downy brome, BROTE), *Lolium multiflorum* Lam. (Italian ryegrass, LOLMU), *Lolium rigidum* (rigid ryegrass), *Lolium multiflorum* subsp. *Gaudini* (annual ryegrass, LOLMG), *Phalaris minor* Retz. (littleseed canarygrass, PHAMI), *Poa annua* L. (annual bluegrass, POAAN), *Setaria pumila* (Poir.) Roemer & J. A. Schultes (yellow foxtail, SETLU), *Setaria viridis* (L.) Beauv. (green foxtail, SETVI), *Amaranthus retroflexus* (redroot pigweed, AMARE), *Chenopodium album* (common lambsquarters, CHEAL), *Cirsium arvense* (L.) Scop. (Canada thistle, CIRAR), *Galium aparine* L. (catchweed bedstraw, GALAP), *Kochia scoparia* (L.) Schrad. (*kochia*, KCHSC), *Lamium purpureum* L. (purple deadnettle, LAMPU), *Matricaria recutita* L. (wild chamomile, MATCH), *Matricaria matricarioides* (Less.) Porter (pineappleweed, MATMT), *Papaver rhoeas* L. (common poppy, PAPRH), *Polygonum convolvulus* L. (wild buckwheat, POLCO), *Salsola tragus* L. (Russian thistle, SASKR), *Sinapis arvensis* (wild mustard, SINAR), *Stellaria media* (L.) Vill. (common chickweed, STEME), *Veronica hederifolia* (Ivy-leaved speedwell, VERHE), *Veronica persica* Poir. (Persian speedwell, VERPE), *Viola arvensis* Murr. (field violet, VIOAR), or *Viola tricolor* L. (wild violet, VIOTR).

In some embodiments, the methods provided herein are utilized to control undesirable vegetation in rice. In certain embodiments, the undesirable vegetation is *Brachiaria platyphylla* (Groseb.) Nash (broadleaf signalgrass, BRAPP), *Digitaria sanguinalis* (L.) Scop. (large crabgrass, DIGSA), *Echinochloa crus-galli* (L.) P. Beauv. (barnyardgrass, ECHCG), *Echinochloa colonum* (L.) LINK (junglerice, ECHCO), *Echinochloa oryzoides* (Ard.) Fritsch (early watergrass, ECHOR), *Echinochloa oryzicola* (Vasinger) Vasinger (late watergrass, ECHPH), *Ischaemum rugosum* Salisb. (saramollagrass, ISCRU), *Leptochloa chinensis* (L.) Nees (Chinese sprangletop, LEFCH), *Leptochloa fascicularis* (Lam.) Gray (bearded sprangletop, LEFFA), *Leptochloa panicoides* (Presl.) Hitchc. (Amazon sprangletop, LEFPA), *Panicum dichotomiflorum* (L.) Michx. (fall *panicum*, PANDI), *Paspalum dilatatum* Poir. (dallisgrass, PASDI), *Cyperus difformis* L. (small-flower flatsedge, CYPDI), *Cyperus esculentus* L. (yellow nutsedge, CYPES), *Cyperus iria* L. (rice flatsedge, CYPIR), *Cyperus rotundus* L. (purple nutsedge, CYPRO), *Eleocharis* species (ELOSS), *Fimbristylis miliacea* (L.) Vahl (globe fringerush, FIMMI), *Schoenoplectus juncoides* Roxb. (Japanese bulrush, SPCJU), *Schoenoplectus maritimus* L. (sea clubrush, SCPMA), *Schoenoplectus mucronatus* L. (ricefield bulrush, SCPMU), *Aeschynomene* species, (jointvetch, AESSS), *Alternanthera philoxeroides* (Mart.) Griseb. (alligatorweed, ALRPH), *Alisma plantago-aquatica* L. (common waterplantain, ALSPA), *Amaranthus* species, (pigweeds and amaranths, AMASS), *Ammannia coccinea* Rottb. (redstem, AMMCO), *Eclipta alba* (L.) Hassk. (American false daisy, ECLAL), *Heteranthera limosa* (SW.) Willd./Vahl (ducksalad, HETLI), *Heteranthera reniformis* R. & P. (roundleaf mudplantain, HETRE), *Ipomoea hederacea* (L.) Jacq. (ivyleaf morningglory, IPOHE), *Lindernia dubia* (L.) Pennell (low false pimpernel, LIDDU), *Monochoria korsakowii* Regel & Maack (*monochoria*, MOOKA), *Monochoria vaginalis* (Burm. F.) C. Presl ex Kuhth, (*monochoria*, MOOVA), *Murdannia nudiflora* (L.) Brenan (doveweed, MUDNU), *Polygonum pensylvanicum* L., (Pennsylvania smartweed, POLPY), *Polygonum persicaria* L. (ladysthumb, POLPE), *Polygonum hydropiperoides* Michx. (POLHP, mild smartweed), *Rotala indica* (Willd.) Koehne (Indian toothcup, ROTIN), *Sagittaria* species (arrowhead, SAGSS), *Sesbania exaltata* (Raf.) Cory/Rydb. Ex Hill (hemp *sesbania*, SEBEX), or *Sphenoclea zeylanica* Gaertn. (gooseweed, SPDZE).

In some embodiments, the methods provided herein are utilized to control undesirable vegetation in range and pasture. In certain embodiments, the undesirable vegetation is *Ambrosia artemisiifolia* L. (common ragweed, AMBEL), *Cassia obtusifolia* (sickle pod, CASOB), *Centaurea maculosa* auct. non Lam. (spotted knapweed, CENMA), *Cirsium arvense* (L.) Scop. (Canada thistle, CIRAR), *Convolvulus arvensis* L. (field bindweed, CONAR), *Euphorbia esula* L. (leafy spurge, EPHES), *Lactuca serriola* L./Torn. (prickly lettuce, LACSE), *Plantago lanceolata* L. (buckhorn plantain, PLALA), *Rumex obtusifolius* L. (broadleaf dock, RUMOB), *Sida spinosa* L. (prickly *sida*, SIDSP), *Sinapis arvensis* L. (wild mustard, SINAR), *Sonchus arvensis* L. (perennial sowthistle, SONAR), *Solidago* species (goldenrod, SOOSS), *Taraxacum officinale* G. H. Weber ex Wiggers (dandelion, TAROF), *Trifolium repens* L. (white clover, TRFRE), or *Urtica dioica* L. (common nettle, URTDI).

In some embodiments, the methods provided herein are utilized to control undesirable vegetation found in row crops. In certain embodiments, the undesirable vegetation is *Alopecurus myosuroides* Huds. (blackgrass, ALOMY), *Avena fatua* L. (wild oat, AVEFA), *Brachiaria platyphylla* (Groseb.) Nash (broadleaf signalgrass, BRAPP), *Digitaria sanguinalis* (L.) Scop. (large crabgrass, DIGSA), *Echinochloa crus-galli* (L.) P. Beauv. (barnyardgrass, ECHCG), *Echinochloa colonum* (L.) Link (junglerice, ECHCO), *Lolium multiflorum* Lam. (Italian ryegrass, LOLMU), *Panicum dichotomiflorum* Michx. (fall *panicum*, PANDI), *Panicum miliaceum* L. (wildproso millet, PANMI), *Setaria faberi* Herrm. (giant foxtail, SETFA), *Setaria viridis* (L.) Beauv. (green foxtail, SETVI), *Sorghum halepense* (L.) Pers. (Johnsongrass, SORHA), *Sorghum bicolor* (L.) Moench ssp. *Arundinaceum* (shattercane, SORVU), *Cyperus esculentus* L. (yellow nutsedge, CYPES), *Cyperus rotundus* L. (purple nutsedge, CYPRO), *Abutilon theophrasti* Medik. (velvetleaf, ABUTH), *Amaranthus* species (pigweeds and amaranths, AMASS), *Ambrosia artemisiifolia* L. (common ragweed, AMBEL), *Ambrosia psilostachya* DC. (western ragweed, AMBPS), *Ambrosia trifida* L. (giant ragweed, AMBTR), *Asclepias syriaca* L. (common milkweed, ASCSY), *Chenopodium album* L. (common lambsquarters, CHEAL), *Cirsium arvense* (L.) Scop. (Canada thistle, CIRAR), *Commelina benghalensis* L. (tropical spiderwort, COMBE), *Datura stramonium* L. (jimsonweed, DATST), *Daucus carota* L. (wild carrot, DAUCA), *Euphorbia heterophylla* L. (wild poinsettia, EPHHL), *Erigeron bonariensis* L. (hairy fleabane, ERIBO), *Erigeron canadensis* L. (Canadian fleabane, ERICA), *Helianthus annuus* L. (common sunflower, HELAN), *Jacquemontia tamnifolia* (L.) Griseb. (smallflower morningglory, IAQTA), *Ipomoea hederacea* (L.) Jacq. (ivyleaf morningglory, IPOHE), *Ipomoea lacunosa* L. (white morningglory, IPOLA), *Lactuca serriola* L./Torn. (prickly lettuce, LACSE), *Portulaca oleracea* L. (common purslane, POROL), *Sida spinosa* L. (prickly *sida*, SIDSP), *Sinapis arvensis* L. (wild mustard, SINAR), *Solanum ptychanthum* Dunal (eastern black nightshade, SOLPT), or *Xanthium strumarium* L. (common cocklebur, XANST).

In certain embodiments, the methods and compositions provided herein are used to control undesirable vegetation, wherein the undesirable vegetation is *Ipomoea, Setaria, Euphorbia, Amaranthus, Cyperus, Chenpodium, Viola, Stellaria*, and/or *Cirsium*.

In certain embodiments, the methods and compositions provided herein are used to control *Ipomoea* hederacea (ivyleaf morningglory, IPOHE), *Setaria faberi* Herrm. (giant foxtail, SETFA), *Abutilon theophrasti* Medik. (velvetleaf, ABUTH), *Euphorbia heterohylla* L. (wild poinsettia, EPHHL), *Amaranthus retroflexus* L. (redroot pigweed, AMARE), *Cyperus esculentus* L. (yellow nutsedge, CYPES), *Chenpodium album* L. (common lambsquarters, CHEAL), *Viola tricolor* L. (wild violet, VIOTR), *Stellaria media* (L.) Vill. (common chickweed, STEME), and/or *Cirsium arvense* (L.) Scop. (Canada thistle, CIRAR).

The compounds of formula I or agriculturally acceptable salts or esters thereof may be used to control herbicide resistant or tolerant weeds. The methods employing the combination of a compound of formula I or agriculturally acceptable salt or ester thereof and the compositions described herein may also be employed to control herbicide resistant or tolerant weeds. Exemplary resistant or tolerant weeds include, but are not limited to, biotypes resistant or tolerant to acetolactate synthase (ALS) inhibitors, photosystem II inhibitors, acetyl CoA carboxylase (ACCase) inhibitors, synthetic auxins, photosystem I inhibitors, 5-enolpyruvylshikimate-3-phosphate (EPSP) synthase inhibitors, microtubule assembly inhibitors, lipid synthesis inhibitors, protoporphyrinogen oxidase (PPO) inhibitors, carotenoid biosynthesis inhibitors, very long chain fatty acid (VLCFA) inhibitors, phytoene desaturase (PDS) inhibitors, glutamine synthetase inhibitors, 4-hydroxyphenyl-pyruvate-dioxygenase (HPPD) inhibitors, mitosis inhibitors, cellulose biosynthesis inhibitors, herbicides with multiple modes-of-action such as quinclorac, and unclassified herbicides such as arylaminopropionic acids, difenzoquat, endothall, and organoarsenicals. Exemplary resistant or tolerant weeds include, but are not limited to, biotypes with resistance or tolerance to multiple herbicides, multiple chemical classes, and multiple herbicide modes-of-action.

In certain embodiments of the compositions and methods described herein, the compound of formula (I) or salt or ester thereof is used in a two component combination with flurtamone. In some embodiments, the two components are used in amounts such that the weight ratio of (a) the compound of formula (I) or salt or ester thereof to (b) flurtamone is from about 1.25-10 of (a) to about 30-250 of (b). As used herein, the weight ratio of the compound of formula (I) or salt or ester thereof to flurtamone, in cases where a salt or ester of the compound of formula (I) is used, refers to the ratio of the acid equivalent weight of said salt or ester to the weight of flurtamone. In certain embodiments, the weight ratio of (a) the compound of formula (I) or salt or ester thereof to (b) flurtamone is from about 1.25-5 of (a) to about 62.5-125 of (b). In one embodiment, the composition comprises (a) the methyl ester of the compound of formula (I) and (b) flurtamone, wherein the weight ratio of the two components is from about 1.25-5 of (a) to about 62.5-125 of (b). In some embodiments, the two components are used in amounts such that the weight ratio of (a) the methyl ester of the compound of formula (I) to (b) flurtamone is 1:6 to 1:200. In some embodiments, the two components are used in amounts such that the weight ratio of (a) the methyl ester of the compound of formula (I) to (b) flurtamone is 1:12.5 to 1:100.

In certain embodiments of the compositions and methods described herein, the compound of formula (I) or salt or ester thereof is used in a three component combination with flurtamone and flufenacet. In some embodiments, the three components are used in amounts such that the weight ratio of (a) the compound of formula (I) or salt or ester thereof to (b) flurtamone to (c) flufenacet is from about 1.25-10 of (a) to about 30-250 of (b) to about 15-120 of (c). In some embodiments, the three components are used in amounts such that the weight ratio of (a) the compound of formula (I) or salt or ester thereof to (b) flurtamone to (c) flufenacet is from about 1.25-5 of (a) to about 62.5-125 of (b) to about 30-60 of (c). In one embodiment, the composition comprises (a) the methyl ester of the compound of formula (I), (b) flurtamone, and (c) flufenacet, wherein the weight ratio of the three components is from about 1.25-5 of (a) to about 62.5-125 of (b) to about 30-60 of flufenacet.

In certain embodiments of the compositions and methods described herein, the compound of formula (I) or salt or ester thereof is used in a three component combination with flurtamone and diflufenican. In some embodiments, the three components are used in amounts such that the weight ratio of (a) the compound of formula (I) or salt or ester thereof to (b) flurtamone to (c) diflufenican is from about 1.25-10 of (a) to about 30-250 of (b) to about 12.5-100 of (c). In certain embodiments, the weight ratio of the compound of formula (I) or salt or ester thereof to (b) flurtamone to (c) diflufenican is from about 1.25-5 of (a) to about 62.5-125 of (b) to about 25-50 of diflufenican. In one embodiment, the composition comprises (a) the methyl ester of the compound of formula (I), (b) flurtamone, and (c) diflufenican, wherein the weight ratio of the three components is from about 1.25-5 of (a) to about 62.5-125 of (b) to about 25-50 of diflufenican.

With respect to the methods, in certain embodiments, the methods comprise contacting the undesirable vegetation or locus thereof with the two or three components or applying the two or three components of a composition described herein to the soil or water to prevent the emergence or growth of vegetation. In some embodiments, the composition is applied at an application rate from about 30 grams active ingredient per hectare (g ai/ha) to about 500 g ai/ha based on the total amount of herbicidal active ingredients in the composition. In certain embodiments, the composition is applied at an application rate from about 60 g ai/ha to about 200 g ai/ha based on the total amount of active ingredients in the composition. In some embodiments, the methods comprise contacting the undesirable vegetation or locus thereof or applying to the soil or water to prevent the emergence or growth of vegetation sequentially or simultaneously with a compound of formula (I) or agriculturally acceptable salt or ester thereof and flurtamone and optionally flufenacet or diflufenican.

In some two component embodiments, flurtamone is applied at a rate from about 30 g ai/ha to about 250 g ai/ha and the compound of formula (I) or salt or ester thereof is applied at a rate from about 1.25 grams acid equivalent per hectare (g ae/ha) to about 10 g ae/ha. In some embodiments, flurtamone is applied at a rate from about 62.5 g ai/ha to about 125 g ai/ha and the compound of formula (I) or salt or ester thereof is applied at a rate from about 1.25 g ae/ha to about 5 g ae/ha. In certain embodiments, the methods utilize the compound of formula (I) or its methyl ester and flurtamone. In one embodiment, the methods utilize the methyl ester of the compound of formula (I) and flurtamone, wherein the methyl ester of the compound of formula (I) is applied at a rate from about 1.25 g ae/ha to about 10 g ae/ha, and flurtamone is applied at a rate from about 62.5 g ai/ha to about 125 g ai/ha.

In some three component embodiments, the compound of formula (I) or salt or ester thereof is applied at a rate from about 1.25 g ae/ha to about 10 g ae/ha, flurtamone is applied at a rate from about 30 g ai/ha to about 250 g ai/ha, and flufenacet is applied at a rate from about 15 g ai/ha to about 120 g ai/ha. In some embodiments, the compound of formula (I) or salt or ester thereof is applied at a rate from about 1.25 g ae/ha to about 5 g ae/ha, the flurtamone is applied at a rate from about 62.5 g ai/ha to about 125 g ai/ha, and flufenacet is applied at a rate from about 30 g ai/ha to about 60 g ai/ha. In certain embodiments, the methods utilize the compound of formula (I) or its methyl ester, flurtamone, and flufenacet. In one embodiment, the methods utilize the methyl ester of the compound of formula (I), flurtamone, and flufenacet wherein the methyl ester of the compound of formula (I) is applied at a rate from about 1.25 g ae/ha to about 5 g ae/ha, flurtamone is applied at a rate from about 62.5 g ai/ha to about 125 g ai/ha, and flufenacet is applied at a rate from about 15 g ai/ha to about 120 g ai/ha.

In some three component embodiments, the compound of formula (I) or salt or ester thereof is applied at a rate from about 1.25 g ae/ha to about 10 g ae/ha, flurtamone is applied at a rate from about 30 g ai/ha to about 250 g ai/ha, and diflufenican is applied at a rate from about 12.5 g ai/ha to about 100 g ai/ha. In some embodiments, the compound of formula (I) or salt or ester thereof is applied at a rate from about 1.25 g ae/ha to about 5 g ae/ha, the flurtamone is applied at a rate from about 62.5 g ai/ha to about 125 g ai/ha, and diflufenican is applied at a rate from about 25 g ai/ha to about 50 g ai/ha. In certain embodiments, the methods utilize the compound of formula (I) or its methyl ester, flurtamone, and diflufenican. In one embodiment, the methods utilize the methyl ester of the compound of formula (I), flurtamone, and diflufenican wherein the methyl ester of the compound of formula (I) is applied at a rate from about 1.25 g ae/ha to about 5 g ae/ha, flurtamone is applied at a rate from about 62.5 g ai/ha to about 125 g ai/ha, and diflufenican is applied at a rate from about 25 g ai/ha to about 50 g ai/ha.

In some embodiments of the methods described herein, the active ingredients are applied simultaneously, including, e.g., in the form of a composition. In some embodiments, the active ingredients are applied sequentially, e.g., within 5, 10, 15, or 30 minutes of each other; 1, 2, 3, 4, 5, 10, 12, 24, 48 hour(s) or each other, or 1 week of each other.

The components of the mixtures described herein can be applied either separately or as part of a multipart herbicidal system.

The mixtures described herein can be applied in conjunction with one or more other herbicides to control a wider variety of undesirable vegetation. When used in conjunction with other herbicides, the composition can be formulated with the other herbicide or herbicides, tank-mixed with the other herbicide or herbicides or applied sequentially with the other herbicide or herbicides. Some of the herbicides that can be employed in conjunction with the compositions and methods described herein include, but are not limited to: 4-CPA, 4-CPB, 4-CPP, 2,4-D, 2,4-D choline salt, 2,4-D esters and amines, 2,4-DB, 3,4-DA, 3,4-DB, 2,4-DEB, 2,4-DEP, 3,4-DP, 2,3,6-TBA, 2,4,5-T, 2,4,5-TB, acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron-methyl, bensulide, benthiocarb, bentazon-sodium, benzadox, benzfendizone, benzipram, benzobicyclon, benzofenap, benzofluor, benzoylprop, benzthiazuron, bicyclopyrone, bifenox, bilanafos, bispyribac-sodium, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone-ethyl, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop-propargyl, clofop, clomazone, clomeprop, cloprop, cloproxydim, clopyralid, cloransulam-methyl, CMA, copper sulfate, CPMF, CPPC, credazine, cresol, cumyluron, cyanatryn, cyanazine, cycloate, cyclosulfamuron, cycloxydim, cycluron, cyhalofop-butyl, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop-methyl, diethamquat, diethatyl, difenopenten, difenoxuron, difenzoquat, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethbenzamide, ethametsulfuron, ethidimuron, ethiolate, ethobenzamid, etobenzamid, ethofumesate, ethoxyfen, ethoxysulfuron, etinofen, etnipromid, etobenzanid, EXD, fenasulam, fenoprop, fenoxaprop, fenoxaprop-P-ethyl, fenoxaprop-P-ethyl+isoxadifen-ethyl, fenoxasulfone, fenquinotrione, fenteracol, fenthiaprop, fentrazamide, fenuron, ferrous sulfate, flamprop, flamprop-M, flazasulfuron, fluazifop, fluazifop-P-butyl, fluazolate, flucarbazone, flucetosulfuron, fluchloralin, flufenicol, flufenpyr-ethyl, flumezin, flumiclorac-pentyl, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, flurochloridone, fluroxypyr, fluthiacet, fomesafen, foramsulfuron, fosamine, fumiclorac, furyloxyfen, glufosinate, glufosinate-ammonium, glufosinate-P-ammonium, glyphosate, halosafen, halosulfuron-methyl, haloxydine, haloxyfop-methyl, haloxyfop-P-methyl, hexachloroacetone, hexaflurate, hexazinone, imazamethabenz, imazamox, imazapic, imazapyr, imazaquin, imazosulfuron, indanofan, indaziflam, iodobonil, iodomethane, iodosulfuron, iodosulfuron-ethyl-sodium, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA esters and amines, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metoxuron, metribuzin, metsulfuron, metsulfuron-methyl, molinate, monalide, monisouron, monochloroacetic acid, monolinuron, monuron, morfamquat, MSMA, naproanilide, napropamide, napropamide-M, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, paraflufenethyl, parafluron, paraquat, pebulate, pelargonic acid, pendimethalin, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron-methyl, procyazine, prodiamine, profluazol, profluralin, profoxydim, proglinazine, prohexadione-calcium, prometon, prometryn, pronamide, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen-ethyl, pyrasulfotole, pyrazogyl, pyrazolynate, pyrazosulfuron-ethyl, pyrazoxyfen, pyribenzoxim, pyributicarb, pyriclor, pyridafol, pyridate, pyriftalid, pyriminobac, pyrimisulfan, pyrithiobac-sodium, pyroxasulfone, quinclorac, quinmerac, quinoclamine, quinonamid, quizalofop, quizalofop-P-ethyl, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosate, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiazafluron, thiazopyr, thidiazimin, thidiazuron, thiencarbazone-methyl, thifensulfuron, thifensulfuron-methyl, thiobencarb, tiocarbazil, tioclorim, topramezone, tralkoxydim, triafamone, tri-allate, triasulfuron, triaziflam, tribenuron, tribenuron-methyl, tricamba, triclopyr choline salt, triclopyr esters and salts, tridiphane, trietazine, trifloxysulfuron, trifluralin, triflusulfuron, trifop, trifopsime, trihydroxytriazine, trimeturon, tripropindan, tritac tritosulfuron, vernolate, xylachlor and salts, esters, optically active isomers and mixtures thereof.

In some embodiments, the compositions described herein are employed in combination with one or more herbicide safeners, such as AD-67 (MON 4660), benoxacor, benthiocarb, brassinolide, cloquintocet (mexyl), cyometrinil, daimuron, dichlormid, dicyclonon, dimepiperate, disulfoton, fenchlorazole-ethyl, fenclorim, flurazole, fluxofenim, furilazole, harpin proteins, isoxadifen-ethyl, jiecaowan, jiecaoxi, mefenpyr-diethyl, mephenate, naphthalic anhydride (NA), oxabetrinil, R29148, 1-[4-(N-(2-methoxybenzoyl)sulfamoyl)phenyl]-3-methylurea, N-(2-methoxybenzoyl)-4-[methylaminocarbonyl)amino]benzenesulfonamide and N-phenyl-sulfonylbenzoic acid amides, to enhance their selectivity. In some embodiments, the safeners are employed in rice, cereal, corn, or maize settings. In some embodiments, the safener is cloquintocet or an ester or salt thereof. In certain embodiments, cloquintocet is utilized to antagonize harmful effects of the compositions on rice and cereals. In some embodiments, the safener is cloquintocet (mexyl).

In some embodiments, compositions provided herein further comprise at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with herbicidal components or other composition ingredients. Such mixtures can be designed for application directly to weeds or their locus or can be concentrates or formulations that are normally diluted with additional carriers and adjuvants before application. They can be solids, such as, for example, dusts, granules, water-dispersible granules, or wettable powders, or liquids, such as, for example, emulsifiable concentrates, solutions, emulsions or suspensions. They can also be provided as a pre-mix or tank mixed.

Suitable agricultural adjuvants and carriers include, but are not limited to, crop oil concentrate; nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99.

Liquid carriers that can be employed include water and organic solvents. The organic solvents include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like; esters of mono, di and polycarboxylic acids and the like. Specific organic solvents include, but are not limited to toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. In certain embodiments, water is the carrier for the dilution of concentrates.

Suitable solid carriers include but are not limited to talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, cellulose, and the like.

In some embodiments, the compositions described herein further comprise one or more surface-active agents. In some embodiments, such surface-active agents are employed in both solid and liquid compositions, and in certain embodiments those designed to be diluted with carrier before application. The surface-active agents can be anionic, cationic or nonionic in character and can be employed as emulsifying agents, wetting agents, suspending agents, or for other purposes. Surfactants which may also be used in the present formulations are described, inter alia, in "McCutcheon's Detergents and Emulsifiers Annual," MC Publishing Corp., Ridgewood, N.J., 1998 and in "Encyclopedia of Surfactants," Vol. I-III, Chemical Publishing Co., New York, 1980-81. Surface-active agents include, but are not limited to salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable or seed oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, and in certain embodiments, methyl esters.

In some embodiments, these materials, such as vegetable or seed oils and their esters, can be used interchangeably as an agricultural adjuvant, as a liquid carrier or as a surface active agent.

Other exemplary additives for use in the compositions provided herein include but are not limited to compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

In some embodiments, the concentration of the active ingredients in the compositions described herein is from about 0.0005 to 98 percent by weight. In some embodiments, the concentration is from about 0.0006 to 90 percent by weight. In compositions designed to be employed as concentrates, the active ingredients, in certain embodiments, are present in a concentration from about 0.1 to 98 weight percent, and in certain embodiments about 0.5 to 90 weight percent. Such compositions are, in certain embodiments, diluted with an inert carrier, such as water, before application. The diluted compositions usually applied to weeds or the locus of weeds contain, in certain embodiments, about 0.0003 to 1.5 weight percent active ingredient and in certain embodiments contain about 0.0008 to 1.0 weight percent.

The present compositions can be applied to weeds or their locus by the use of conventional ground or aerial dusters, sprayers, and granule applicators, by addition to irrigation or paddy water, and by other conventional means known to those skilled in the art.

The described embodiments and following examples are for illustrative purposes and are not intended to limit the scope of the claims. Other modifications, uses, or combinations with respect to the compositions described herein will be apparent to a person of ordinary skill in the art without departing from the spirit and scope of the claimed subject matter.

Examples

Results in Tables 1-12 are greenhouse trial results for foliar applied compositions. The compositions tested, application rates employed, plant species tested, and results are given in Tables 1-12.

The following abbreviations are used in Tables 1-12:

| | | |
|---|---|---|
| TRZAS | *Triticum aestivum* (spring) | spring wheat |
| IPOHE | *Ipomoea hederacea* | ivyleaf morningglory |
| SETFA | *Setaria faberi* Herrm. | giant foxtail |
| ABUTH | *Abutilon theophrasti* Medik. | velvetleaf |
| EPHHL | *Euphorbia heterohylla* L. | wild poinsettia |
| AMARE | *Amaranthus retroflexus* L. | redroot pigweed |
| CYPES | *Cyperus esculentus* L. | yellow nutsedge |
| CHEAL | *Chenpodium album* L. | common lambsquarters |
| VIOTR | *Viola tricolor* L. | wild violet |
| STEME | *Stellaria media* (L.) Vill. | common chickweed |
| CIRAR | *Cirsium arvense* (L.) Scop. | Canada thistle | g/ha=grams acid equivalent per hectare for Cmpd 1 and grams active ingredient per hectare for flurtamone, flufenacet, and diflufenican Obs=observed value Exp=expected value as calculated by the equations set forth above.

Cmpd 1=methyl 4-amino-3-chloro-6-(4-chloro-2-fluoro-3-methoxyphenyl)-pyridine-2-carboxylate

TABLE 1

Synergistic activity of Cmpd 1 plus flurtamone, and Cmpd 1 plus flurtamone and diflufenican

| Application Rate (g/ha) | | | TRZAS | | IPOHE | | SETFA | | ABUTH | |
|---|---|---|---|---|---|---|---|---|---|---|
| Cmpd 1 | Flurtamone | Diflufenican | Obs | Exp | Obs | Exp | Obs | Exp | Obs | Exp |
| 1.25 | | | 0 | — | 15 | — | 0 | — | 78 | — |
| 0 | 62.5 | | 0 | — | 25 | — | 0 | — | 40 | — |
| 0 | 125 | | 0 | — | 33 | — | 10 | — | 63 | — |
| 1.25 | 62.5 | | 0 | 0 | 68 | 36 | 0 | 0 | 88 | 87 |
| 1.25 | 125 | | 0 | 0 | 78 | 43 | 0 | 10 | 93 | 92 |
| 0 | | 25 | 0 | — | 10 | — | 8 | — | 15 | — |
| 0 | | 50 | 0 | — | 13 | — | 5 | — | 15 | — |
| 1.25 | | 25 | 0 | 0 | 33 | 24 | 25 | 8 | 96 | 81 |
| 1.25 | | 50 | 0 | 0 | 35 | 26 | 50 | 5 | 98 | 81 |
| 1.25 | 62.5 | 25 | 0 | 0 | 80 | 43 | 5 | 8 | 97 | 89 |
| 1.25 | 125 | 50 | 0 | 0 | 70 | 50 | 5 | 15 | 100 | 93 |

TABLE 2

Synergistic activity of Cmpd 1 plus flurtamone, and Cmpd 1 plus flurtamone and diflufenican

| Application Rate (g/ha) | | | EPHHL | | AMARE | | CYPES | | CHEAL | | VIOTR | | STEME | | CIRAR | |
|---|---|---|---|---|---|---|---|---|---|---|---|---|---|---|---|---|
| Cmpd 1 | Flurtamone | Diflufenican | Obs | Exp | Obs | Exp | Obs | Exp | Obs | Exp | Obs | Exp | Obs | Exp | Obs | Exp |
| 1.25 | | | 60 | — | 30 | — | 58 | — | 60 | — | 5 | — | 20 | — | 20 | — |
| 0 | 62.5 | | 25 | — | 40 | — | 5 | — | 25 | — | 25 | — | 20 | — | 88 | — |
| 0 | 125 | | 40 | — | 65 | — | 8 | — | 40 | — | 30 | — | 30 | — | 95 | — |
| 1.25 | 62.5 | | 88 | 70 | 88 | 58 | 60 | 60 | 88 | 70 | 50 | 29 | 40 | 36 | 88 | 90 |
| 1.25 | 125 | | 92 | 76 | 95 | 76 | 30 | 61 | 98 | 76 | 70 | 34 | 68 | 44 | 93 | 96 |
| 0 | | 25 | 43 | — | 25 | — | 0 | — | 25 | — | 10 | — | 10 | — | 28 | — |
| 0 | | 50 | 50 | — | 50 | — | 0 | — | 25 | — | 15 | — | 15 | — | 25 | — |
| 1.25 | | 25 | 85 | 77 | 83 | 48 | 65 | 58 | 89 | 70 | 45 | 15 | 73 | 28 | 85 | 42 |
| 1.25 | | 50 | 83 | 80 | 85 | 65 | 70 | 58 | 96 | 70 | 50 | 19 | 70 | 32 | 88 | 40 |
| 1.25 | 62.5 | 25 | 93 | 83 | 88 | 69 | 83 | 60 | 96 | 78 | 38 | 36 | 63 | 42 | 92 | 93 |
| 1.25 | 125 | 50 | 99 | 88 | 98 | 88 | 68 | 61 | 100 | 82 | 81 | 43 | 73 | 52 | 96 | 97 |

TABLE 3

Synergistic activity of Cmpd 1 plus flurtamone, and Cmpd 1 plus flurtamone and diflufenican

| Application Rate (g/ha) | | | TRZAS | | IPOHE | | SETFA | | ABUTH | |
|---|---|---|---|---|---|---|---|---|---|---|
| Cmpd 1 | Flurtamone | Diflufenican | Obs | Exp | Obs | Exp | Obs | Exp | Obs | Exp |
| 2.50 | | | 0 | — | 15 | — | 5 | — | 91 | — |
| 2.50 | 62.5 | | 0 | 0 | 83 | 36 | 10 | 5 | 100 | 95 |

TABLE 3-continued

Synergistic activity of Cmpd 1 plus flurtamone, and Cmpd 1 plus flurtamone and diflufenican

| Application Rate (g/ha) | | | TRZAS | | IPOHE | | SETFA | | ABUTH | |
|---|---|---|---|---|---|---|---|---|---|---|
| Cmpd 1 | Flurtamone | Diflufenican | Obs | Exp | Obs | Exp | Obs | Exp | Obs | Exp |
| 2.50 | 125 | | 0 | 0 | 90 | 43 | 5 | 15 | 100 | 97 |
| 2.50 | | 25 | 0 | 0 | 45 | 24 | 15 | 12 | 99 | 92 |
| 2.50 | | 50 | 0 | 0 | 68 | 26 | 35 | 10 | 100 | 92 |
| 2.50 | 62.5 | 25 | 0 | 0 | 83 | 43 | 15 | 12 | 99 | 95 |
| 2.50 | 125 | 50 | 5 | 0 | 68 | 50 | 15 | 19 | 98 | 97 |

TABLE 4

Synergistic activity of Cmpd 1 plus flurtamone, and Cmpd 1 plus flurtamone and diflufenican

| Application Rate (g/ha) | | | EPHHL | | AMARE | | CYPES | | CHEAL | | VIOTR | | STEME | | CIRAR | |
|---|---|---|---|---|---|---|---|---|---|---|---|---|---|---|---|---|
| Cmpd 1 | Flurtamone | Diflufenican | Obs | Exp | Obs | Exp | Obs | Exp | Obs | Exp | Obs | Exp | Obs | Exp | Obs | Exp |
| 2.50 | | | 89 | — | 93 | — | 85 | — | 83 | — | 15 | — | 58 | — | 55 | — |
| 2.50 | 62.5 | | 91 | 92 | 91 | 96 | 85 | 86 | 100 | 87 | 70 | 36 | 83 | 66 | 90 | 94 |
| 2.50 | 125 | | 97 | 93 | 95 | 97 | 65 | 86 | 99 | 90 | 65 | 41 | 63 | 70 | 94 | 98 |
| 2.50 | | 25 | 96 | 94 | 93 | 94 | 91 | 85 | 96 | 87 | 73 | 24 | 73 | 62 | 88 | 67 |
| 2.50 | | 50 | 95 | 95 | 93 | 96 | 79 | 85 | 95 | 87 | 70 | 28 | 75 | 64 | 90 | 66 |
| 2.50 | 62.5 | 25 | 94 | 95 | 90 | 97 | 78 | 86 | 98 | 90 | 70 | 43 | 70 | 69 | 94 | 96 |
| 2.50 | 125 | 50 | 100 | 97 | 98 | 99 | 86 | 86 | 100 | 92 | 77 | 49 | 78 | 75 | 93 | 98 |

TABLE 5

Synergistic activity of Cmpd 1 plus flurtamone and Cmpd 1 plus flurtamone and diflufenican

| Application Rate (g/ha) | | | TRZAS | | IPOHE | | SETFA | | ABUTH | |
|---|---|---|---|---|---|---|---|---|---|---|
| Cmpd 1 | Flurtamone | Diflufenican | Obs | Exp | Obs | Exp | Obs | Exp | Obs | Exp |
| 5.00 | | | 0 | — | 35 | — | 0 | — | 98 | — |
| 5.00 | 62.5 | | 0 | 0 | 93 | 51 | 0 | 0 | 99 | 99 |
| 5.00 | 125 | | 0 | 0 | 88 | 56 | 5 | 10 | 98 | 99 |
| 5.00 | | 25 | 0 | 0 | 73 | 42 | 40 | 8 | 99 | 98 |
| 5.00 | | 50 | 0 | 0 | 53 | 43 | 50 | 5 | 100 | 98 |
| 5.00 | 62.5 | 25 | 0 | 0 | 18 | 56 | 65 | 8 | 99 | 99 |
| 5.00 | 125 | 50 | 0 | 0 | 25 | 62 | 60 | 15 | 100 | 99 |
| | 62.5 | 25 | 0 | — | 28 | — | 8 | — | 15 | — |
| | 125 | 50 | 0 | — | 25 | — | 18 | — | 65 | — |

TABLE 6

Synergistic activity of Cmpd 1 plus flurtamone and Cmpd 1 plus flurtamone and diflufenican

| Application Rate (g/ha) | | | EPHHL | | AMARE | | CYPES | | CHEAL | | VIOTR | | STEME | | CIRAR | |
|---|---|---|---|---|---|---|---|---|---|---|---|---|---|---|---|---|
| Cmpd 1 | Flurtamone | Diflufenican | Obs | Exp | Obs | Exp | Obs | Exp | Obs | Exp | Obs | Exp | Obs | Exp | Obs | Exp |
| 5.00 | | | 92 | — | 78 | — | 81 | — | 85 | — | 23 | — | 65 | — | 75 | — |
| 5.00 | 62.5 | | 95 | 94 | 91 | 87 | 78 | 82 | 95 | 89 | 75 | 42 | 80 | 72 | 95 | 97 |
| 5.00 | 125 | | 100 | 95 | 100 | 92 | 85 | 82 | 100 | 91 | 83 | 46 | 88 | 76 | 96 | 99 |
| 5.00 | | 25 | 95 | 95 | 94 | 83 | 88 | 81 | 95 | 89 | 65 | 30 | 75 | 69 | 94 | 82 |
| 5.00 | | 50 | 92 | 96 | 92 | 89 | 93 | 81 | 95 | 89 | 78 | 34 | 73 | 70 | 94 | 81 |
| 5.00 | 62.5 | 25 | 94 | 96 | 94 | 90 | 95 | 82 | 99 | 92 | 84 | 48 | 83 | 75 | 95 | 98 |
| 5.00 | 125 | 50 | 98 | 97 | 97 | 96 | 93 | 82 | 99 | 93 | 75 | 54 | 83 | 79 | 96 | 99 |
| | 62.5 | 25 | 30 | — | 30 | — | 0 | — | 65 | — | 35 | — | 35 | — | 83 | — |
| | 125 | 50 | 50 | — | 58 | — | 0 | — | 65 | — | 45 | — | 25 | — | 94 | — |

TABLE 7

Synergistic activity of Cmpd 1 plus flurtamone and Cmpd 1 plus flurtamone and flufenacet

| Application Rate (g/ha) | | | TRZAS | | IPOHE | | SETFA | | ABUTH | |
|---|---|---|---|---|---|---|---|---|---|---|
| Cmpd 1 | Flurtamone | Flufenacet | Obs | Exp | Obs | Exp | Obs | Exp | Obs | Exp |
| 1.25 | | | 0 | — | 15 | — | 0 | — | 78 | — |
| 0 | 62.5 | | 0 | — | 25 | — | 0 | — | 40 | — |
| 0 | 125 | | 0 | — | 33 | — | 10 | — | 63 | — |
| 1.25 | 62.5 | | 0 | 0 | 68 | 36 | 0 | 0 | 88 | 87 |
| 1.25 | 125 | | 0 | 0 | 78 | 43 | 0 | 10 | 93 | 92 |
| 0 | | 30 | 0 | — | 0 | — | 0 | — | 0 | — |
| 0 | | 60 | 0 | — | 0 | — | 0 | — | 0 | — |
| 1.25 | | 30 | 0 | 0 | 20 | 15 | 0 | 0 | 90 | 78 |
| 1.25 | | 60 | 0 | 0 | 25 | 15 | 0 | 0 | 94 | 78 |
| 1.25 | 62.5 | 30 | 0 | 0 | 30 | 36 | 5 | 0 | 93 | 87 |
| 1.25 | 125 | 60 | 0 | 0 | 68 | 43 | 5 | 10 | 98 | 92 |

TABLE 8

Synergistic activity of Cmpd 1 plus flurtamone and Cmpd 1 plus flurtamone and flufenacet

| Application Rate (g/ha) | | | EPHHL | | AMARE | | CYPES | | CHEAL | | VIOTR | | STEME | | CIRAR | |
|---|---|---|---|---|---|---|---|---|---|---|---|---|---|---|---|---|
| Cmpd 1 | Flurtamone | Flufenacet | Obs | Exp | Obs | Exp | Obs | Exp | Obs | Exp | Obs | Exp | Obs | Exp | Obs | Exp |
| 1.25 | | | 60 | — | 30 | — | 58 | — | 60 | — | 5 | — | 20 | — | 20 | — |
| 0 | 62.5 | | 25 | — | 40 | — | 5 | — | 25 | — | 25 | — | 20 | — | 88 | — |
| 0 | 125 | | 40 | — | 65 | — | 8 | — | 40 | — | 30 | — | 30 | — | 95 | — |
| 1.25 | 62.5 | | 88 | 70 | 88 | 58 | 60 | 60 | 88 | 70 | 50 | 29 | 40 | 36 | 88 | 90 |
| 1.25 | 125 | | 92 | 76 | 95 | 76 | 30 | 61 | 98 | 76 | 70 | 34 | 68 | 44 | 93 | 96 |
| 0 | | 30 | 0 | — | 0 | — | 0 | — | 0 | — | 0 | — | 0 | — | 0 | — |
| 0 | | 60 | 0 | — | 0 | — | 0 | — | 0 | — | 0 | — | 0 | — | 0 | — |
| 1.25 | | 30 | 80 | 60 | 80 | 30 | 75 | 58 | 90 | 60 | 35 | 5 | 73 | 20 | 60 | 20 |
| 1.25 | | 60 | 80 | 60 | 79 | 30 | 78 | 58 | 94 | 60 | 30 | 5 | 60 | 20 | 63 | 20 |
| 1.25 | 62.5 | 30 | 91 | 70 | 88 | 58 | 68 | 60 | 95 | 70 | 45 | 29 | 68 | 36 | 86 | 90 |
| 1.25 | 125 | 60 | 96 | 76 | 96 | 76 | 80 | 61 | 94 | 76 | 63 | 34 | 65 | 44 | 92 | 96 |

TABLE 9

Synergistic activity of Cmpd 1 plus flurtamone and Cmpd 1 plus flurtamone and flufenacet

| Application Rate (g/ha) | | | TRZAS | | IPOHE | | SETFA | | ABUTH | |
|---|---|---|---|---|---|---|---|---|---|---|
| Cmpd 1 | Flurtamone | Flufenacet | Obs | Exp | Obs | Exp | Obs | Exp | Obs | Exp |
| 2.50 | | | 0 | — | 15 | — | 5 | — | 91 | — |
| 2.50 | 62.5 | | 0 | 0 | 83 | 36 | 10 | 5 | 100 | 95 |
| 2.50 | 125 | | 0 | 0 | 90 | 43 | 5 | 15 | 100 | 97 |
| 2.50 | | 30 | 0 | 0 | 15 | 15 | 0 | 5 | 95 | 91 |
| 2.50 | | 60 | 0 | 0 | 20 | 15 | 0 | 5 | 100 | 91 |
| 2.50 | 62.5 | 30 | 0 | 0 | 65 | 36 | 5 | 5 | 97 | 95 |
| 2.50 | 125 | 60 | 0 | 0 | 73 | 43 | 0 | 15 | 99 | 97 |

TABLE 10

Synergistic activity of Cmpd 1 plus flurtamone and Cmpd 1 plus flurtamone and flufenacet

| Application Rate (g/ha) | | | EPHHL | | AMARE | | CYPES | | CHEAL | | VIOTR | | STEME | | CIRAR | |
|---|---|---|---|---|---|---|---|---|---|---|---|---|---|---|---|---|
| Cmpd 1 | Flurtamone | Flufenacet | Obs | Exp | Obs | Exp | Obs | Exp | Obs | Exp | Obs | Exp | Obs | Exp | Obs | Exp |
| 2.50 | | | 89 | — | 93 | — | 85 | — | 83 | — | 15 | — | 58 | — | 55 | — |
| 2.50 | 62.5 | | 91 | 92 | 91 | 96 | 85 | 86 | 100 | 87 | 70 | 36 | 83 | 66 | 90 | 94 |
| 2.50 | 125 | | 97 | 93 | 95 | 97 | 65 | 86 | 99 | 90 | 65 | 41 | 63 | 70 | 94 | 98 |

TABLE 10-continued

Synergistic activity of Cmpd 1 plus flurtamone and Cmpd 1 plus flurtamone and flufenacet

| Application Rate (g/ha) | | | EPHHL | | AMARE | | CYPES | | CHEAL | | VIOTR | | STEME | | CIRAR | |
|---|---|---|---|---|---|---|---|---|---|---|---|---|---|---|---|---|
| Cmpd 1 | Flurtamone | Flufenacet | Obs | Exp | Obs | Exp | Obs | Exp | Obs | Exp | Obs | Exp | Obs | Exp | Obs | Exp |
| 2.50 | | 30 | 90 | 89 | 85 | 93 | 83 | 85 | 90 | 83 | 75 | 15 | 73 | 58 | 80 | 55 |
| 2.50 | | 60 | 93 | 89 | 78 | 93 | 90 | 85 | 94 | 83 | 73 | 15 | 70 | 58 | 83 | 55 |
| 2.50 | 62.5 | 30 | 93 | 92 | 85 | 96 | 70 | 86 | 97 | 87 | 60 | 36 | 58 | 66 | 88 | 94 |
| 2.50 | 125 | 60 | 94 | 93 | 98 | 97 | 70 | 86 | 99 | 90 | 65 | 41 | 68 | 70 | 90 | 98 |

TABLE 11

Synergistic activity of Cmpd 1 plus flurtamone and Cmpd 1 plus flurtamone and flufenacet

| Application Rate (g/ha) | | | TRZAS | | IPOHE | | SETFA | | ABUTH | |
|---|---|---|---|---|---|---|---|---|---|---|
| Cmpd 1 | Flurtamone | Flufenacet | Obs | Exp | Obs | Exp | Obs | Exp | Obs | Exp |
| 5.00 | | | 0 | — | 35 | — | 0 | — | 98 | — |
| 5.00 | 62.5 | | 0 | 0 | 93 | 51 | 0 | 0 | 99 | 99 |
| 5.00 | 125 | | 0 | 0 | 88 | 56 | 5 | 10 | 98 | 99 |
| 5.00 | | 30 | 0 | 0 | 20 | 35 | 5 | 0 | 93 | 98 |
| 5.00 | | 60 | 0 | 0 | 25 | 35 | 63 | 0 | 90 | 98 |
| 5.00 | 62.5 | 30 | 0 | 0 | 78 | 51 | 20 | 0 | 94 | 99 |
| 5.00 | 125 | 60 | 0 | 0 | 50 | 56 | 28 | 10 | 98 | 99 |
| 0 | 62.5 | 30 | 0 | — | 33 | — | 0 | — | 20 | — |
| 0 | 125 | 60 | 0 | — | 35 | — | 0 | — | 45 | — |

TABLE 12

Synergistic activity of Cmpd 1 plus flurtamone and Cmpd 1 plus flurtamone and flufenacet

| Application Rate (g/ha) | | | EPHHL | | AMARE | | CYPES | | CHEAL | | VIOTR | | STEME | | CIRAR | |
|---|---|---|---|---|---|---|---|---|---|---|---|---|---|---|---|---|
| Cmpd 1 | Flurtamone | Flufenacet | Obs | Exp | Obs | Exp | Obs | Exp | Obs | Exp | Obs | Exp | Obs | Exp | Obs | Exp |
| 5.00 | | | 92 | — | 78 | — | 81 | — | 85 | — | 23 | — | 65 | — | 75 | — |
| 5.00 | 62.5 | | 95 | 94 | 91 | 87 | 78 | 82 | 95 | 89 | 75 | 42 | 80 | 72 | 95 | 97 |
| 5.00 | 125 | | 100 | 95 | 100 | 92 | 85 | 82 | 100 | 91 | 83 | 46 | 88 | 76 | 96 | 99 |
| 5.00 | | 30 | 88 | 92 | 80 | 78 | 85 | 81 | 89 | 85 | 60 | 23 | 60 | 65 | 84 | 75 |
| 5.00 | | 60 | 90 | 92 | 85 | 78 | 95 | 81 | 99 | 85 | 65 | 23 | 68 | 65 | 82 | 75 |
| 5.00 | 62.5 | 30 | 98 | 94 | 95 | 87 | 95 | 82 | 98 | 89 | 75 | 42 | 92 | 72 | 85 | 97 |
| 5.00 | 125 | 60 | 99 | 95 | 94 | 92 | 90 | 82 | 99 | 91 | 68 | 46 | 90 | 76 | 92 | 99 |
| 0 | 62.5 | 30 | 30 | — | 15 | — | 0 | — | 75 | — | 45 | — | 20 | — | 73 | — |
| 0 | 125 | 60 | 30 | — | 30 | — | 0 | — | 45 | — | 35 | — | 35 | — | 85 | — |

What is claimed is:

1. A herbicidal composition comprising a synergistic herbicidally effective amount of the combination of (a) a compound of formula (I)

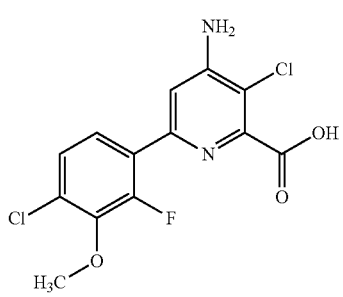

(I)

or an agriculturally acceptable salt or ester thereof and (b) flurtamone, wherein the composition does not contain glufosinate, L-glufosinate, or bialaphos.

2. The herbicidal composition of claim 1, further comprising flufenican as a third herbicidal active component.

3. The herbicidal composition of claim 1, further comprising diflufenican as a third herbicidal active component.

4. The composition of claim 1, wherein (a) is a $C_{1-4}$ alkyl or benzyl ester of compound of formula (I).

5. The composition of claim 1, wherein (a) is a methyl ester of the compound of formula (I).

6. The composition of claim 1, further comprising a herbicide safener.

7. The composition of claim 1 wherein (a) is the methyl ester of the compound of formula (I) and the weight ratio of (a) to (b) is from about 1.25-10 of (a) to about 30-250 of (b).

8. The composition of claim 1, wherein the weight ratio of (a) to (b) is from about 1.25-5 of (a) to about 62.5-125 of (b).

9. The composition of claim 1, further comprising (c) flufenacet as a third herbicidally active component, and wherein (a) is the methyl ester of the compound of formula (I) and the weight ratio of (a) to (b) to (c) is from about 1.25-10 of (a) to about 30-250 of (b) to about 15-120 of (c).

10. The composition of claim 1, further comprising (c) flufenacet as a third herbicidally active component, and wherein (a) is the methyl ester of the compound of formula (I) and the weight ratio of (a) to (b) to (c) is from about 1.25-5 of (a) to about 62.5-125 of (b) to 30-60 of (c).

11. The composition of claim 1, further comprising (c) diflufenican as a third herbicidally active component and wherein (a) is the methyl ester of the compound of formula (I) and the weight ratio of (a) to (b) to (c) is from about 1.25-10 of (a) to about 30-250 of (b) to about 12.5-100 of (c).

12. The composition of claim 1, further comprising (c) diflufenican as a third herbicidally active component, and wherein (a) is the methyl ester of the compound of formula (I) and the weight ratio of (a) to (b) to (c) is from about 1.25-10 of (a) to about 62.5-125 of (b) to about 25-50 of (c).

13. The composition of claim 1, further comprising an agriculturally acceptable adjuvant or carrier.

14. A method of controlling undesirable vegetation which comprises applying to an area comprising undesirable vegetation a herbicidally effective amount of the composition of claim 1.

15. A method of controlling undesirable vegetation which comprises applying to an area comprising undesirable vegetation a synergistic herbicidally effective amount of a combination comprising the following herbicidally active components: (a) a compound of formula (I)

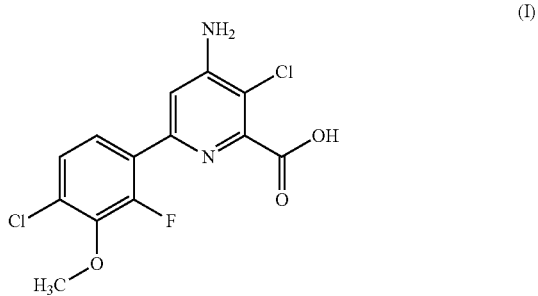 [SMILES: COc1c(Cl)ccc(-c2cc(N)c(Cl)c(C(=O)O)n2)c1F]

or an agriculturally acceptable salt or ester thereof and (b) flurtamone, wherein no glufosinate, L-glufosinate, or bialaphos is applied.

16. The method of claim 15, wherein the undesirable vegetation is controlled in rice, wheat, triticale, barley, oats, rye, corn, maize, cereals, pastures, grasslands, rangelands, fallow-land, and, industrial vegetation management or rights-of-way.

17. The method of claim 15, wherein the undesirable vegetation is immature.

18. The method of claim 15, wherein the herbicidally active components are applied pre-emergently.

19. The method of claim 15, wherein the herbicidally active components are applied post-emergently.

20. The method of claim 15, wherein the undesirable vegetation is controlled in glyphosate-, glufosinate-, dicamba-, phenoxy auxins-, pyridyloxy auxins-, aryloxyphenoxypropionates-, acetyl CoA carboxylase (ACCase) inhibitors-, imidazolinones-, acetolactate synthase (ALS) inhibitors-, 4-hydroxyphenyl-pyruvate dioxygenase (HPPD) inhibitors-, protoporphyrinogen oxidase (PPO) inhibitors-, triazines-, or bromoxynil-tolerant crop.

21. The method of claim 15 wherein (a) is the methyl ester of the compound of formula (I), and the (a) and (b) are applied in a weight ratio of (a) to (b) of from about 1.25-10 of (a) to about 30-250 of (b).

22. The method of claim 15 wherein (a) is the methyl ester of the compound of formula (I), and the (a) and (b) are applied in a weight ratio of (a) to (b) of from about 1.25-5 of (a) to about 62.5-125 of (b).

23. The method of claim 15, further comprising (c) diflufenican as a third herbicidally active component.

24. The method of claim 23, wherein (a) is the methyl ester of the compound of formula (I), and the (a) and (b) and (c) are applied in a weight ratio of (a) to (b) to (c) of from about 1.25-10 of (a) to about 30-250 of (b) to about 12.5-100 of (c).

25. The method of claim 23, wherein (a) is the methyl ester of the compound of formula (I), and the (a) and (b) and (c) are applied in a weight ratio of (a) to (b) to (c) of from about 1.25-5 of (a) to about 62.5-125 of (b) to about 25-50 of (c).

26. The method of claim 15, further comprising (c) flufenacet as a third herbicidally active component.

27. The method of claim 26 wherein (a) is the methyl ester of the compound of formula (I), and the (a) and (b) and (c) are applied in a weight ratio of (a) to (b) to (c) of from about 1.25-10 of (a) to about 30-250 of (b) to about 15-120 of (c).

28. The method of claim 26 wherein (a) is the methyl ester of the compound of formula (I), and the (a) and (b) and (c) are applied in a weight ratio of (a) to (b) to (c) of from about 1.25-5 of (a) to about 62.5-125 of (b) to about 25-50 of (c).

29. The method of claim 26 wherein (a) is the methyl ester of the compound of formula (I), and the (a) and (b) and (c) are applied in a weight ratio of (a) to (b) to (c) of from about 1.25-5 of (a) to about 62.5-125 of (b) to about 30-60 of (c).

30. The method of claim 26, wherein the undesirable vegetation is *Ipomoea, Setaria, Euphorbia, Amaranthus, Cyperus, Chenpodium, Viola, Stellaria,* or *Cirsium*.

31. The method of claim 26, wherein the undesirable vegetation is IPOHE, SETFA, ABUTH, EPHHL, AMARE, CYPES, CHEAL, VIOTR, STEME, or CIRAR.

* * * * *